United States Patent
Razzano

(10) Patent No.: US 6,521,218 B1
(45) Date of Patent: Feb. 18, 2003

(54) WATERBORNE COLORED AND CLEAR COAT FINGERNAIL POLISH

(76) Inventor: Dominick D. Razzano, 107 Westward Dr., Miami Springs, FL (US) 33166

( * ) Notice: Subject to any disclaimer, the term of this patent is extended or adjusted under 35 U.S.C. 154(b) by 0 days.

(21) Appl. No.: 10/166,420

(22) Filed: Jun. 10, 2002

Related U.S. Application Data

(63) Continuation-in-part of application No. 10/100,257, filed on Mar. 15, 2002.

(51) Int. Cl.⁷ .................................................. A61K 7/04
(52) U.S. Cl. ........................................................ 424/61
(58) Field of Search ................................... 424/61, 401

(56) References Cited

U.S. PATENT DOCUMENTS 5,935,590 A * 8/1999 Razzano ..................... 424/401
5,989,575 A * 11/1999 Razzano ..................... 424/401

* cited by examiner

*Primary Examiner*—Thurman K. Page
*Assistant Examiner*—S. Howard
(74) *Attorney, Agent, or Firm*—Robert M. Downey, P.A.

(57) ABSTRACT

A waterborne composition for application to fingernails, toenails and acrylic nails by brush or spray is disclosed. The composition includes an emulsified resin binder, coalescents, plasticizers and one or more colored pigments. The composition is non-flammable, odorless, fast drying and environmentally safe. All ingredients in the composition are non-toxic.

3 Claims, No Drawings

WATERBORNE COLORED AND CLEAR COAT FINGERNAIL POLISH

This application is a continuation-in-part of Ser. No. 10/100,257 filed Mar. 15, 2002.

BACKGROUND OF THE INVENTION

1. Field of the Invention

This invention relates to waterborne clear and pigmented nail polish and, more particularly, to a waterborne organic resin composition for nail polish comprising an emulsified non-toxic binder and a non-toxic pigment.

2. Discussion of the Related Art

The nail polishes used today are based on nitrocellulose as the resin binder and a number of compounds which are considered toxic, including formaldehyde and toluene. Also a high amount (70%) of flammable solvents which have strong odors and various degrees of toxicity are necessary for solubizing the nitrocellulose. The present invention was developed to eliminate all the disadvantages of the organic solvent system by using water as the solvent. Also, the use of the phenylethylene-acrylic. copolymer (Tg°C.=40±10°) to replace the nitrocellulose which necessitated organic flammable and strong odor organic solvents to be put in solution.

ADVANTAGES OF THE INVENTION

The waterborne fingernail polish composition of the present invention has the following advantages over the current nitrocellulose-based nail polish which has been on the market for at least sixty years:

1. Non-flammable
2. Odorless.
3. Non-toxic
4. Minimal effect on the ozone layer.
5. Lower insurance rates for shipping due to its non-flammability.
6. Simpler to manufacture than present nitrocellulose solvent type.
7. Less probability of allergic reaction because its free of volatile pungent solvents.
8. Water based fingernail polish eliminates danger of explosions during manufacture.
9. Less chipping of polish off the fingernail after 10 days on the nails.
10. Considerably less (if any) pollution of atmosphere than present product on the market.

SUMMARY OF THE INVENTION

The present invention is directed to a waterborne clear or colored pigment liquid applied by brush or spray to fingernails, toenails and artificial nails. The waterborne fingernail polish composition includes an emulsified resin binder, coalescents, plasticizers, and colored pigments. In a preferred embodiment, the emulsified resin binder is a phenyl acrylic co-polymer resin. (Tg°C.=40±10°)

Chemical plasticizers are used in this product to provide the necessary flexibility of the. nail polish in order to avoid chipping off the fingernail after a week or ten days on the nail. The ones that were satisfactory and non-toxic were Butlyl Benzyl Phthalate, 2 Ethyl Hexyl Diphenyl Phosphate, 1 butyl phenyl diphenyl phosphate, triphenyl phosphate.

In use, two coats of the colored pigmented composition are applied to the nail surface and allowed to dry for 1–3 minutes, depending on ambient temperature and humidity. To protect the applied film of colored fingernail polish, one coat of clear waterborne composition is applied, allowing 5–10 minutes of drying time between application of the clear coat to avoid softening the colored coat underneath.

DETAILED DESCRIPTION OF THE PREFERRED EMBODIMENTS

The waterborne organic resin composition of the present invention is intended for application to fingernails, toenails and acrylic artificial nails. The composition comprises an emulsified non-toxic binder in combination with one or more non-toxic pigments which are approved by the U.S. Food and Drug Administration for use in nail polish. The composition further includes coalescents which function to fuse together precipitates (i.e. binder resin particles) into a uniform, smooth and level film when coats of the composition are applied to the surface of fingernails, toenails, and acrylic artificial nails and allowed to air dry. The coalescents further provide good flow-out leveling of film upon drying. In the preferred embodiment, the coalescents include propylene glycol methyl propyl ether acetate. Other non-toxic coalescents which can be used in the compostion include: N-methyl-2-pyrrolidone, propylene glycol N propyl ether propylene glycol methyl ether; di-propylene glycol methyl ether; tri-propylene glycol methyl ether; and propylene glycol methyl ether acetate. Plasticizers are included to give the dried film flexibility.

The elimination of volatile solvents replaced by water in the composition results in a nonflammable nail polish. Further elimination of volatile solvents provides a more environmentally friendly nail polish product which does not pollute the atmosphere.

The waterborne nail polish composition consists of two formulas. The first formula is a color-producing resin composition. The second formula is a clear waterborne topcoat resin composition to protect the underlying coats of color resin compositions and to further enhance the gloss of the dried color resin composition.

Preparation of Waterborne Colored and Clear Coat Fingernail Polish

EXAMPLE 1

I. Colored Coat (Red DCC Red 30—SunChemical)

Part A

| Ingredients | Lbs | Gals | N.V.M. | Lbs. Dry Pigment |
|---|---|---|---|---|
| A. Phenylethylene - acrylic Copolymer | 709.90 | 82.26 | 326.55 | — |
| B. Coalescent & Plasticizer Emulsion | 56.98 | 6.58 | 32.64 | — |
| C. Red Pigment Dispersion (RND C30 SunChem) | 125.02 | 13.16 | 52.51 | 37.13 |
| | 891.90 | 102.00 | 411.70 | 37.13 |

Manufacturing Procedures (First prepare Part B)
1. Prepare a predetermined quantity (store extra for future use), of the Coalescent and Plasticizer emulsion B shown as two solutions:

PART B

|  | Lbs | Gals | Lbs N.V.M. |
|---|---|---|---|
| Oil Phase: | | | |
| Propylene glycol methyl ether acetate | 200.75 | 25.00 | 200.75 |
| Butyl Benzyl Phthalate | 242.50 | 25.00 | 242.50 |
| | 443.25 | 50.00 | 443.25 |
| Water Phase: | | | |
| Distilled water | 330.60 | 40.00 | 0.00 |
| *Nonionic Surfactant (Air Products & Chemical Co.) | 89.90 | 10.00 | 53.04 |
| | 410.50 | 50.00 | 53.04 |
| TOTAL | 866.75 | 100.00 | 496.29 |

*75% Ethoxlated 2,4,7,9 Tetramethyl Decyn - 4-7 DIOL

Bring together under strong agitation, the oil phase to the water phase. Completed Viscosity and Wt/Gal are 15" No2 Zahn—25° and 8.6 Lbs.

To complete the formulation, add the phenylethylene-acrylic copolymer slowly with agitation to the coalescent and plasticizer emulsion. Finally add the pigment dispersion.

The Part A final physical and chemical constants are:

| Viscosity | 25"–27" No. 2 ZAHN @ 25° |
|---|---|
| Wt/Gal | 8.14 lbs. |
| pH | 8–10 |

EXAMPLE 2

II. Clear Coat Fingernail Polish

| Ingredients | Lbs | Gals | N.V.M. | Properties |
|---|---|---|---|---|
| 1. Phenylethylene - acrylic Copolymer | 799.05 | 92.59 | 367.56 | Viscosity = 25" No. 2 ZAHN @ 25° C. |
| 2. Coalescent & Plasticizer Emulsion | 63.80 | 7.41 | 36.55 | Lbs/Gal = 8.6 Lbs. = 46.8% pH = 7 ± 0.5 |
| | 862.85 | 100.00 | 404.11 | |

Preparation: Slowly add #2 to #1 Under Slow Agitation

While the instant invention has been shown and described in accordance with preferred and practical embodiments thereof, it is recognized that departures from the instant disclosure are contemplated within the spirit and scope of the present invention, as defined in the following claims under the doctrine of equivalents.

What is claimed is:

1. A nail polish composition comprising:

an emulsified non-toxic resin binder comprising a phenyl acrylic copolymer having a glass transition of between 30° C. and 50° C.

at least one non-toxic coalescent;

at least one non-toxic plasticizer;

at least one non-toxic color pigment; and water.

2. The nail polish composition as recited in claim 1 wherein said at least one coalescent is selected from the group consisting of:

propylene glycol N propyl ether;

N methyl-2-pyrrolidone;

propylene glycol methyl ether;

di-propylene glycol methyl ether;

tri-propylene glycol methyl ether; and propylene glycol methyl ether acetate.

3. The nail polish composition as recited in claim 1 comprising a combination of coalescents and one or more of the following plasticizers selected from the group consisting of:

butyl benzyl phthalate;

2-ethylhexyl diphenyl phosphate;

1-butylphenyl diphenyl phospate; and triphenyl phosphate.

\* \* \* \* \*

UNITED STATES PATENT AND TRADEMARK OFFICE
CERTIFICATE OF CORRECTION

PATENT NO.    : 6,521,218 B1
DATED         : February 18, 2003
INVENTOR(S)   : Dominick D. Razzano It is certified that error appears in the above-identified patent and that said Letters Patent is hereby corrected as shown below:

<u>Title page,</u>
Item [76], the address of the inventor should read as follows:

-- Dominick D. Razzano
      5902 N.W. 40th Terrace
      Virginia, Gardens, FL 33166 --

Signed and Sealed this

Seventeenth Day of June, 2003

JAMES E. ROGAN
*Director of the United States Patent and Trademark Office*